United States Patent
Woodbury et al.

(10) Patent No.: US 9,719,951 B1
(45) Date of Patent: Aug. 1, 2017

(54) METHOD AND APPARATUS FOR MOISTURE DETECTION

(71) Applicant: Helvetia Wireless LLC, Scottsdale, AZ (US)

(72) Inventors: Brian C. Woodbury, Gilbert, AZ (US); Roc Lastinger, Cave Creek, AZ (US)

(73) Assignee: Helvetia Wireless LLC, Scottsdale, AZ (US)

( * ) Notice: Subject to any disclaimer, the term of this patent is extended or adjusted under 35 U.S.C. 154(b) by 300 days.

(21) Appl. No.: 14/327,882

(22) Filed: Jul. 10, 2014

Related U.S. Application Data (60) Provisional application No. 61/845,459, filed on Jul. 12, 2013.

(51) Int. Cl.
*G01N 27/02* (2006.01)
*G01B 7/32* (2006.01)
*G01B 7/00* (2006.01)
*G01N 27/04* (2006.01)

(52) U.S. Cl.
CPC .......... *G01N 27/048* (2013.01); *G01B 7/003* (2013.01); *G01B 7/32* (2013.01)

(58) Field of Classification Search
None
See application file for complete search history.

(56) References Cited

U.S. PATENT DOCUMENTS

| | | |
|---|---|---|
| 2,737,615 A | 3/1956 | Roby |
| 3,145,567 A | 8/1965 | Bobrowsky |
| 4,319,232 A | 3/1982 | Westphal |
| 4,350,968 A | 9/1982 | Tokarz |
| 4,386,231 A | 5/1983 | Vokey |
| 4,411,155 A | 10/1983 | Coulange |
| 4,594,638 A | 6/1986 | Suzuki |
| 4,677,371 A | 6/1987 | Imaizumi |
| 4,928,513 A | 5/1990 | Sugihara |
| 5,220,514 A | 6/1993 | John |
| 5,235,286 A | 8/1993 | Masia |
| 5,275,044 A | 1/1994 | Riley |
| 5,570,030 A | 10/1996 | Wightman |
| 5,698,083 A | 12/1997 | Glass |
| 6,175,310 B1 | 1/2001 | Gott |
| 6,787,718 B2 | 9/2004 | Andberg |
| 7,292,155 B2 | 11/2007 | Vokey |

(Continued)

FOREIGN PATENT DOCUMENTS

| | | |
|---|---|---|
| CA | 2312368 | 4/2000 |
| EP | 558057 | 9/1993 |

(Continued)

*Primary Examiner* — Melissa Koval
*Assistant Examiner* — Felicia Farrow
(74) *Attorney, Agent, or Firm* — Letham Law Firm LLC; Lawrence Letham (57) ABSTRACT

A method and apparatus for detecting moisture that includes at least three conductors. One of the conductors has a different resistance than the other conductors. A liquid extends between the conductors. The difference between the impedance through a pair of conductors and the liquid and the impedance of through another pair of conductors and the liquid may be used to determine the position of the liquid along a length of the conductors. Similar methods may be used to determine an area of a liquid with respect to the conductors.

8 Claims, 6 Drawing Sheets

(56) References Cited

U.S. PATENT DOCUMENTS

| | | |
|---|---|---|
| 7,688,215 B2 | 3/2010 | Vokey |
| 2005/0165369 A1 | 7/2005 | Hodge |
| 2005/0225335 A1 | 10/2005 | Filipkowski |
| 2005/0255724 A1 | 11/2005 | Picco |
| 2009/0158819 A1 | 6/2009 | Vincent |
| 2009/0218223 A1 | 9/2009 | Manaresi |
| 2010/0127848 A1 | 5/2010 | Mustapha |
| 2010/0176827 A1* | 7/2010 | Yamazaki ............ G01N 27/125 324/699 |
| 2010/0241094 A1 | 9/2010 | Sherron |
| 2010/0319435 A1 | 12/2010 | Strong |
| 2011/0179861 A1 | 7/2011 | Grange |
| 2012/0251859 A1 | 10/2012 | Payne |
| 2013/0075018 A1 | 3/2013 | Heppe |
| 2013/0150769 A1 | 6/2013 | Heppe |

FOREIGN PATENT DOCUMENTS

| | | |
|---|---|---|
| EP | 563809 | 10/1993 |
| EP | 1751302 | 2/2007 |
| GB | 2218837 | 11/1989 |
| WO | 8900681 | 1/1989 |
| WO | 0000801 | 1/2000 |
| WO | 2006086178 | 8/2006 |
| WO | 2009018650 | 2/2009 |
| WO | 2010064753 | 6/2010 |

\* cited by examiner

METHOD AND APPARATUS FOR MOISTURE DETECTION

FIELD OF THE INVENTION

Embodiments of the present invention relate to moisture sensors and processing circuits related to moisture sensors.

BACKGROUND OF THE INVENTION

Previous moisture detection systems, utilized two closely spaced conductors (e.g., conductive elements). When a conductive liquid (e.g., water, urine, blood, body fluid) is present, an electrical circuit (e.g., connections, path) between two conductors may be established and may be detected by a reader (e.g., circuit, detector).

The impedance through the liquid can vary widely due to factors that include conductor spacing, amount of liquid (e.g., moisture), and chemical content of the liquid.

The variation in the impedance through the liquid may reduce the accuracy of detecting a position (e.g., length, distance, location) of the liquid with respect to the conductor. Detecting moisture may benefit from improvements in reducing the effect of variation in the impedance of a liquid on accuracy, detecting the location of the liquid, and detecting an area of the liquid.

DETAILED DESCRIPTION OF THE PREFERRED EMBODIMENTS

A moisture detector may detect the presence of moisture (e.g., liquid, vapor). A moisture detector may detect a position of moisture relative to the structure of the moisture detector. A moisture detector may detect an area (e.g., spread, extend) of moisture.

Figure 1:
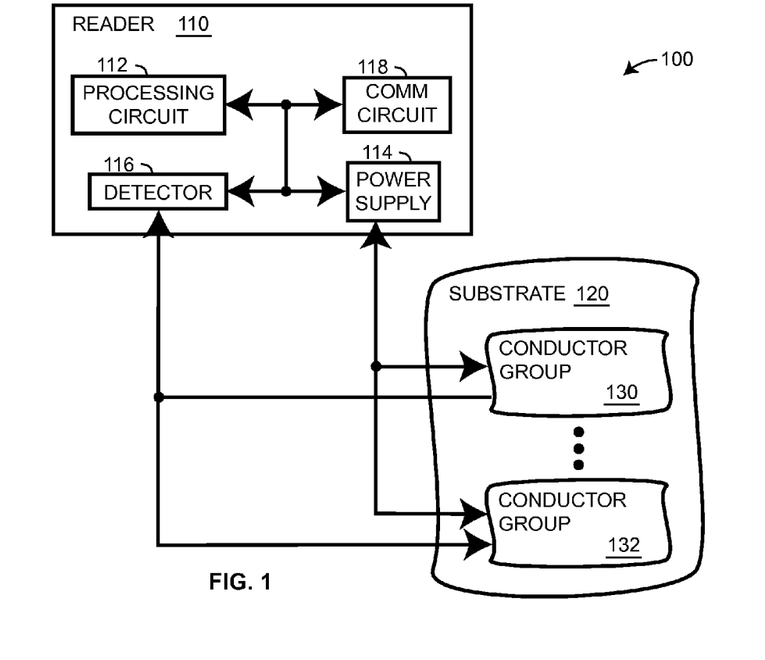
FIG. 1 is a functional diagram of a moisture detector in accordance with various aspects of the present invention.

Moisture detector 100 may include reader 110, substrate 120, and conductor groups 130-132. A conductor group may include three or more conductors as discussed below. Conductors groups may operate independently of each other or cooperate to detect a presence of moisture, a location of moisture, and/or an area of moisture as discussed below. A reader may include processing circuit 112 and a power supply 114. A reader may further include detectors 116. The function of detectors 116 may be performed in whole or in part by processing circuit 112. A reader may further include communication circuit 118.

According to various aspects of the present invention, a moisture detector includes at least three conductors that cooperate to detect the presence of a liquid, determine the location of the liquid with respect to the conductors and/or the substrate, and determine the amount of area, relative to the conductors and/or the substrate, that is covered by the liquid.

A conductor may be formed of any conductive material. Conductive material may include a metal and/or semi-conductive (e.g., semi-conductor) material. The structure (e.g., form, form factor) of a conductor may include any conventional structure of a conductor. Structures of a conductor may include the form of a conventional wire, a thin-film conductor, a thick-film conductor, and a deposited (e.g., printed, formed by deposition) conductive material.

A conductor may have an impedance (e.g., resistance). The impedance of a conductor may include the bulk resistivity of the material of the conductor (e.g., $\rho$, rho), sheet resistance of the material of the conductor, and a total resistance of the conductor.

Conductors whose impedance include a sheet resistance may have a width, a thickness, a length, and a bulk resistivity $\rho$ (e.g., rho). Sheet resistance Rs is defined as the resistivity $\rho$ divided by the thickness of the conductor. Sheet resistance is expressed as $\Omega/\square$ (e.g., ohms/square, ohms per square). In equation form, Rs is:

$$Rs = \rho/t, \text{ where } a \quad \text{Equation 1:}$$

$\rho$ (e.g., rho) is the resistivity of the conductor, as discussed above.

t is the thickness of the conductor. An example of a conductor having a sheet resistance and a thickness shown in FIG. 3. Conductors 230-260 have width 334, 344, 354, and 364 and thickness 332, 342, 352, and 362 respectively. An impedance of a conductor having a sheet resistance or an impedance per unit length may be proportional to a length of the conductor. The length of conductors 230-260 is length 310. A total resistance of conductors 230-260 is proportional to length 310.

A total resistance of a conductor may be determined (e.g., calculated) in accordance with the sheet resistance of the material of the conductor, a width of the material of the conductor, and a length of the material of the conductor. The total resistance of a conductor may be expressed as:

$$R = Rs*(L/W) \quad \text{Equation 2:}$$

Figure 3:
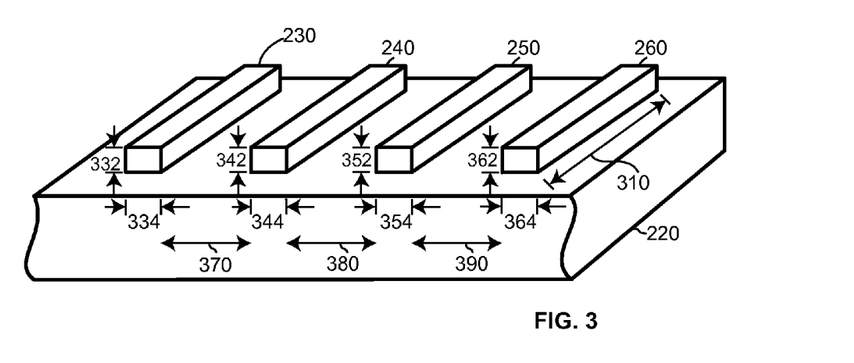
FIG. 3 is a perspective plan view the substrate and conductors of FIG. 2.

The total resistance of conductors 230-260 may be calculated as:

$$R230 = Rs230*(\text{length } 310/\text{width } 334);$$

$$R240 = Rs240*(\text{length } 310/\text{width } 344);$$

$$R250 = Rs250*(\text{length } 310/\text{width } 354); \text{ and}$$

$$R260 = Rs260*(\text{length } 310/\text{width } 364); \text{ where}$$

Rs230, Rs240, Rs250, and Rs260 is the sheet resistance of the material that forms conductor 230, 240, 250, and 260 respectively.

Length 310 is the length of each of the conductors, which in this example all conductors have the same length.

Width 334, 344, 354, and 364 are the widths of conductors 230, 240, 250, and 260 respectively, which may be the same or different.

R230, R240, R250, R260 are the resistance (e.g., impedance) of the conductors 230, 240, 250, and 260 respectively along the entire length of the conductor.

The total resistance of a conductor may be measured (e.g., detected, determined) by applying a voltage across the conductor, measuring the current through the conductor, and determining the resistance of the conductor. A current used to determine the total resistance of a conductor may enter one end of the conductor, travel the length of the conductor, and exit the other end of the conductor.

According to various aspect of the present invention, at least one conductor of the at least three conductors has a total impedance (e.g., resistance) that is different form the total impedance of the other two conductors.

A sheet resistance and/or a total resistance of a conductor may be more or less than a sheet resistance and/or a total resistance of a liquid that is between two or more conductors.

A substrate may position conductors relative to each other. Any one conductor may be positioned proximate to any number of other conductors. The spacing between any two or more conductors may be uniform or variable. Conductor spacing may be selected in accordance with the conductive properties of a liquid. Conductors may be spaced apart from each other so that that liquid between the conductors present an impedance (e.g., resistance) with in a desired range. Conductor spacing may be selected in accordance with a viscosity of a liquid. For example, conductors for detecting a low viscosity liquid may be spaced closely together so that the point (e.g., location, position) where the liquid intersects one conductor will be close to the point where the liquid intersects the other conductors. A lesser distance between conductors encourages a liquid move between conductors rather than spreading (e.g., traveling) a length of one conductor without spreading to the other conductors.

A substrate may be formed of layers of materials. The layers of the materials may be the same and/or different. A conductor may be positioned in or on any layer of the material of a substrate. A conductor may be covered, above and/or below, with a layer of the substrate. A conductor may be coupled to a substrate using any conventional method (e.g., printing, deposition, mechanical) for coupling. A substrate may insulate conductors from each other in the absence of a liquid.

A substrate may absorb, resist penetration of, and/or repel a liquid. A material of a substrate may facilitate the uniform spread of a liquid through the substrate. A material of a substrate may retard the movement of (e.g., absorb) a liquid through the substrate. A substrate may influence the movement of a liquid through and/or across the substrate. A substrate may facilitate movement of a liquid toward and/or between conductors.

A substrate may perform other functions in addition to the functions discussed above. A substrate may protect a surface (e.g., mattress, bed, wheel chair) from a liquid. A substrate may improve sanitation by being disposable after use. A substrate may provide comfort to a patient (e.g., wick moisture away, retain moisture in a location) in a hospital. A substrate may retain a moisture, when present, in an area. A substrate may form the material of clothing for a human. A substrate may function as an insulator. A substrate may perform the function of a protective barrier.

A substrate may include electronic circuits positioned in and/or on the substrate. A substrate may include electronic infrastructure (e.g., buses, power, ground) for electrically coupling to electronic circuits. A substrate may include structure for coupling mechanically and/or electrically to conductors and/or a reader.

A reader may detect the presence of a liquid. A reader may detect a position of a liquid along a length of a conductor. A reader may detect an area of a liquid. A reader may detect a current flow through a circuit that may include some or all of a conductor, the substrate, and the liquid. A reader may electrically couple to one or more conductors. A reader may apply a voltage across one or more conductors. A reader may detect a current flow through a conductor, a substrate, and/or a liquid. A reader may detect an impedance of a conductor, a liquid, a substrate or a combination thereof.

A reader may determine a physical property of a conductor, a substrate and/or a liquid. A physical property may include capacitance, inductance, temperature, and impedance. For example, a reader may determine a physical property of a liquid, a substrate, or a combination of the liquid and the substrate. A reader may determine a type of a liquid.

A power supply may mechanically and/or electrically couple to one or more conductors. A power supply of a reader may provide a voltage across one or more conductors, a substrate, and/or a liquid. A power supply may provide a current to one or more conductors, a substrate, and/or a liquid. A power supply may report a magnitude of a provided voltage and/or current. A power supply may include any conventional power supply, power supply technology (e.g., solar cells), and/or battery.

A detector and/or a processing circuit may mechanically and/or electrically couple to one or more conductors. A detector and/or a processing circuit may detect a current that flows through one or more conductors, a substrate, and/or a liquid. A detector and/or a processing circuit may detect a voltage applied across one or more conductors, a substrate, and/or a liquid. A detector and/or a processing circuit may report a magnitude of a detected current and/or voltage. A detector may include any conventional circuit and/or sensor for detecting a voltage and/or a current.

A processing circuit may perform any conventional type of calculation (e.g., add, subtract, multiply, divide, integrate) and/or conversion (e.g., AtoD, DtoA, scale, invert). A processing circuit may store information. A processing circuit may detect physical properties (e.g., temperature, voltage, current, time). A processing circuit may perform a calculation using detected and/or stored information. A processing circuit may provide a result of detecting, calculator, and/or converting. A processing circuit may perform a function in accordance with a result of a calculation, a result of a conversion, and/or a physical property detected. A processing circuit may include any conventional circuit for performing the functions of a processing circuit including converters, sensors, microprocessors, signal processors, relays, op amps, comparators.

A communication circuit may communicate electronically. A communication circuit may send information to and/or receive information (e.g., data) electronically. A communication circuit may use any conventional protocol and circuits for communicating. A communication circuit may receive information for controlling the moisture sensor via a communication. A processing circuit may receive information from a communication circuit. A processing circuit may perform a function in accordance with information received via a communication circuit. A processing circuit may provide information for transmission to a communication circuit. A processing circuit may control the operation of and/or cooperate with the communication circuit to perform the functions of communication. A processing circuit may perform all or some of the functions of a communication circuit.

A processing circuit may provide a report. A report may include an electronic notice, an audible sound, a flashing light, a printed message. An electronic notice may include a packet of data for communication via a conventional network, a text message for communication via a conventional cell phone network, an electronic signal that conveys information. Subject matter of a report may include a notice of detected moisture, a notice of no detected moisture, a notice of a fault of the reader, substrate, and/or conductor, a position of detected moisture, an area of detected moisture. A report may be provided to a communication circuit for transmission.

Figure 2:
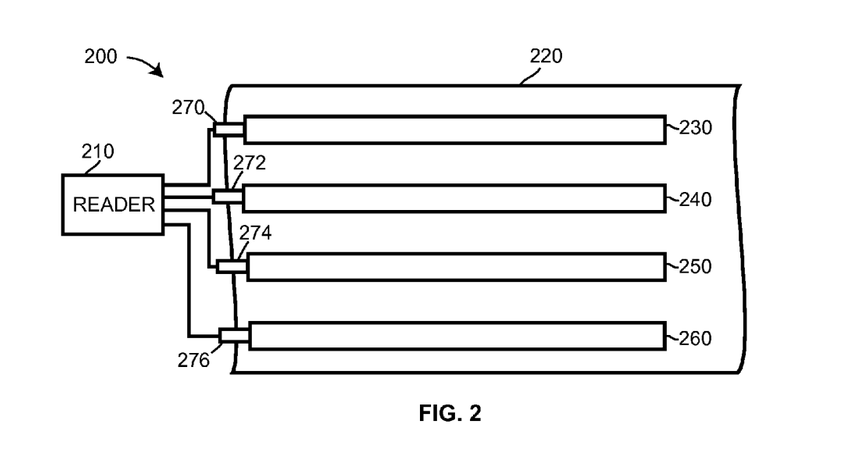
FIG. 2 is a top plan view of an implementation of a moisture detector according to various aspects of the present invention.
Figure 4:
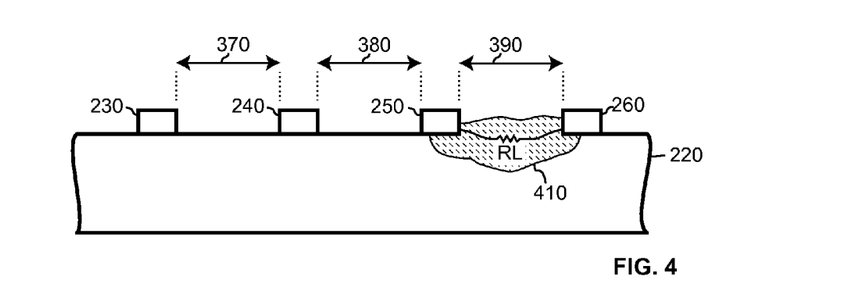
FIG. 4 is a side plan view the substrate and conductors FIG. 2 in the presence of moisture.

For example, moisture detecting system 200 of FIGS. 2-4, includes reader 210, substrate 220, and conductors 230-260. Conductors 230-260 are positioned on substrate 220. In an implementation, substrate 220 is an absorbent (e.g., hygroscopic) pad for use on hospital beds.

Tabs 270-276 facilitate the coupling of reader 210 to conductors 230-260. Tabs may include any conventional leads, clips, connectors, and/or couplers. Tabs may be integral to substrate 220, integral to conductors 230-260, or a portion of the wires (e.g., leads, conductors) from reader 210. Preferably, the resistance of tabs 270-276 is significantly (e.g., orders of magnitude if possible) less than conductors 230-260 and/or the resistance of any liquid that may be detected.

In an implementation, conductors 230-260 are formed of a thin film. In another implementation, conductors 230-260 are formed by printing a resistive ink on substrate 220. An resistance per unit length and the total resistance of conductors 230-260 may be in accordance with the sheet resistance of the material used to form the conductors.

Inks (e.g., resistive inks, polymer thick film) used for printing conductors on a substrate may include silver ink, which may have a sheet resistance as low as 8 milliohms per square (e.g., 0.008 ohms per square), carbon ink, which may have a sheet resistance as high as 2000 ohms per square, and mixtures thereof. Resistive inks may include copper inks. In an implementation, a resistive ink used to form conductors has a impedance of 200 milliohms per square.

Conductors 230-260 may have the same or different width (e.g., 334, 344, 354, 364), thickness (e.g., 332, 342, 352, 362), length (e.g., 310), and $\rho$.

In an implementation, conductors 230 and 260 have the same total resistance (e.g., R1) and conductors 240 and 250 have the same total resistance (e.g., R2), but the sheet resistance of conductors 230 and 260 is different from the total resistance of conductors 240 and 250. The resistivity $\rho$ or thickness of a conductor may be changed to modify the sheet resistance of the conductor to accomplish different total resistances. In an implementation, conductors 230 and 260 are formed using a material having a first $\rho$ while conductors 240 and 250 are formed using a material having a second $\rho$ that is different from the first $\rho$. Using materials having a different bulk resistivity $\rho$ enables conductors 230-260 to have the same width, thickness, and length, yet provide the different total resistances discussed above.

In an implementation, the total resistance (e.g., R230, R260) of conductors 230 and 260 are the same and the total resistance (e.g., R240, R250) of conductors 240 and 250 are the same, but the total resistance of conductors 230 and 260 is different from the resistance of conductors 240 and 250. The length and/or width of a conductor may be change to modify the total resistance of a conductor. In an implementation, conductors 230-260 all have the same length, conductors 230 and 260 have the same width, conductors 240 and 250 have the same width, but the width of conductors 230 and 260 is different from the width of conductors 240 and 250.

Two conductors may be used to detect a presence of a liquid. A liquid that spreads (e.g., spans, contacts, bridges) between two conductors may establish a finite (e.g., not infinite, not open circuit) impedance between the conductors. When no liquid bridges between the two conductors, the magnitude of the impedance between conductors is large (e.g., infinite, open circuit) and no electrical circuit may be established between the two conductors. When no electrical circuit exits between two conductors, it is likely that there is no liquid between the two conductors.

For example, no liquid bridges between conductors 230, 240, and/or 250, so the impedance between conductors 230, 240, and/or 250 is infinite. Liquid 410 spans between conductors 250 and 260. Liquid 410 also permeates a portion of the substrate between conductors 250 and 260. Because liquid 410 is conductive, liquid 410 establishes finite impedance RL between conductors 250 and 260. Applying a voltage across (e.g., between) conductors 250 and 260 establishes a voltage across RL which permits a current to travel between conductors 250 and 260 via impedance RL. The impedance RL between conductors enables reader 210 to detect the presence of liquid (e.g., moisture).

When a liquid spreads between two or more conductors, a uniform distance between conductors increases the likelihood that the impedance of the liquid between conductors is the same. The distance between conductors and/or the material of the substrate proximate to conductors may be such that a liquid will more likely spread between proximate conductors rather than spreading only along a length of one conductor. Since the impedance of the liquid between the conductors (e.g., RL) permits reader 210 to detect moisture, conductors spacing or substrate material that facilitates the spread of a liquid between conductors facilitates detecting moisture.

Figure 5:
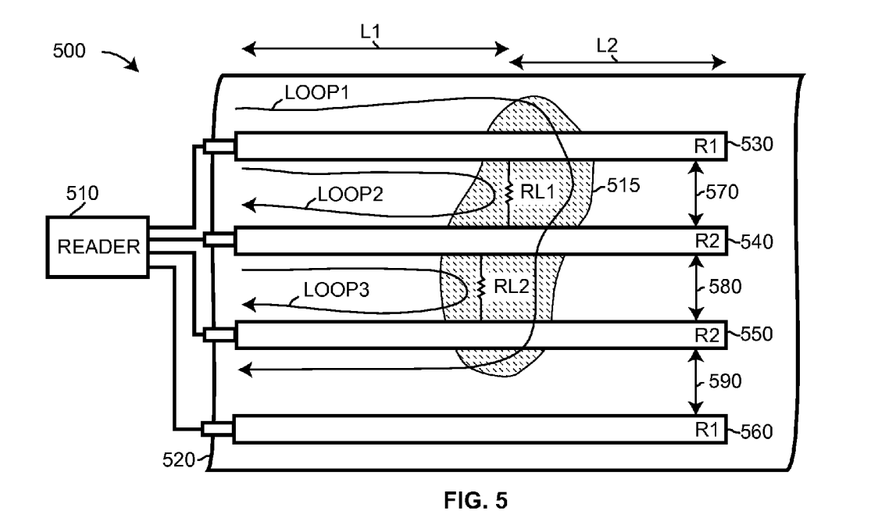
FIG. 5 is a top plan view of an implementation of a moisture detector in the presence of moisture according to various aspects of the present invention.

In an implementation of a moisture detecting system, system 500, referring to FIG. 5, the distance between conductors 530 and 540 (e.g., 570), conductors 540 and 550 (e.g., 580), and conductors 550 and 560 (e.g., 590) is approximately the same. The total resistance (e.g., impedance) of a conductor in this implementation is the resistance as measure from the end of the conductor proximate to reader 510 along the length of the conductor to the end of the conductor distal from reader 510.

The total resistance of conductor 530 (e.g., R530) and conductor 560 (e.g., R560) is the same (e.g., R1). The total resistance of conductor 540 (e.g., R540) and conductor 550 (e.g., R550) is the same (e.g., R2). The total resistance of conductors 530 and 560 is different from the total resistance of conductors 540 and 550 (e.g., R1≠R2). Further, as discussed above, the total resistance of at least one conductor of any three conductors (e.g., 530, 540, 550, 560) selected is different. The difference in the total resistance of the conductors may be due to the factors (e.g., Rs, width) discussed above.

Liquid 515 spans from conductor 530 to conductor 550 establishing impedances RL1 and RL2 through the liquid between conductors 530 and 540 and conductors 540 and 550 respectively. Liquid 515 may or may not permeate substrate 520.

To detect whether a liquid is present, reader 510 may apply a voltage to conductors 530-560 and detect the resulting current. For example, reader 510 applies a voltage across conductors 530 and 540. Because impedance RL1 exits between conductors 530 and 540 a current flows in loop2 thereby indicating the presence of a liquid to reader 510. The reader may also apply a voltage across conductors 540 and 550 and because impedance RL2 exits between conductors 540 and 550, a current flows in loop3 thereby informing reader 510 of the presence of a liquid. Reader 510 may also applied a voltage across conductors 530 and 550 to detect a current that flows in loop1 through impedances RL1 and RL2 thereby detecting the presence of a liquid.

Reader 510 may apply a voltage across conductors 530 and 560, 540 and 560, or 550 and 560; however, because the liquid does not reach conductor 560, no electrical path exists between conductors 530-550 and conductor 560, so reader 510 detects (e.g., determines) that there is no liquid between conductors 530-550 and conductor 560.

According to various aspects of the present invention, reader 510 may also detect (e.g., determine, measure, calculate) the position of liquid 515 with respect to the length of two or more conductors. For example, reader 510 may detect that the location of liquid 515 is a distance L1 along the length of conductors 530-540. To detect the position of the liquid, reader 510 applies a voltage across conductors 530 and 540, measures the current that flows, and calculates the impedance of loop2. The impedance of loop2 may be expressed as:

$$R\text{loop2} = R530\_along\_L1 + RL1 + R540\_along\_L1,$$
where
Equation 3:

Rloop2: is the impedance along the loop from reader 510 along length L1 of conductor 530 through the impedance RL1 and along the length L1 of conductor 540 back to reader 510.

R530_along_L1 is the impedance along length L1 of conductor 530.

RL1 is the impedance through the liquid between conductor 530 and conductor 540.

R540_along_L1 is the impedance along length L1 of conductor 540.

Because the impedance RL1 of liquid 515 short circuits conductors 530 and 540, the impedance of the entire length (e.g., L1+L2) of conductor 530 or 540 is not part of the circuit of loop2. Current from reader 510 flows only through the L1 portion of the conductors.

The depiction of length L1 in FIG. 4 is not intended to be exact. Because reader 510 is attached to the left side of the conductors, with respect to FIG. 5, length L1 will likely be toward the left side of the pool of liquid 515, as opposed to the middle of the pool or right side of the pool. Length L1 will be the distance from the left side of the conductors to the portion of liquid 515 that provides (e.g., establishes) an electrical coupling (e.g., via resistances RL1 and RL2) between conductors 530, 540, and 550. Establishing resistances RL1 and RL2 may depend on the material of the substrate, the amount of saturation of the substrate, the conductivity of the liquid, the shape (e.g., flat, concave, convex) of the substrate, and the separation of the conductors.

Reader 510 further applies a voltage across conductors 540 and 550, measures the current that flows, and calculates the impedance of loop3. The impedance of loop3 may be expressed as:

$$R\text{loop3} = R540\_along\_L1 + RL2 + R550\_along\_L1,$$
where
Equation 4:

Rloop3: is the impedance along the loop from reader 510 along length L1 of conductor 540 through the impedance RL2 and along the length L1 of conductor 550 back to reader 510.

R540_along_L1 is the impedance along length L1 of conductor 540.

RL2 is the impedance through the liquid between conductor 540 and conductor 550.

R550_along_L1 is the impedance along length L1 of conductor 550.

According to various aspects of the present invention, reader 510 may take the difference of the impedance of loop2 and loop3. The difference may be expressed as:

$$R\text{loop2} - R\text{loop3} = R530\_along\_L1 + RL1 + R540\_along\_L1 - (R540\_along\_L1 + RL2 + R550\_along\_L1).$$
Equation 5:

In this implementation, the distance between conductors 530 and 540 (e.g., 570) and the distance between conductors 540 and 550 (e.g., 580) is about the same. A further assumption is that impedance of liquid 515 is substantially uniform. Because the distances 570 and 580 are about the same and the impedance of liquid 515 is substantially uniform throughout, the magnitude of impedance RL1 and RL2 are the about same. Positioning conductors at equal intervals provides the advantage that when the difference of two loops is determined, the resistances (e.g., RL1, RL2) due to the liquid cancel out. Using the above information and assumptions, the difference of the impedance of loop2 and loop3 simplifies to:

$$R\text{loop2} - R\text{loop3} = R530\_along\_L1 - R550\_along\_L1.$$
Equation 6:

As discussed above, the resistance of conductor 530 is different from the resistance of conductor 550, so the value of the above equation is a finite number and not zero.

As discussed above, the resistance of a conductor that has a sheet resistance is given by Equation 2 (e.g., R=Rs*(L/W)). In this example, the length of Equation 2 is length L1 because the current in either loop2 or loop3 travels only along length L1 and not the entire length of the conductor (e.g., L1+L2). Substitution of Equation 2 into Equation 6 yields:

$$R\text{loop2} - R\text{loop3} = Rs530*(L1/W530) - Rs550*(L1/W550),$$ where
Equation 7:

Rloop2−Rloop3: is the difference of the magnitudes of the impedances of loop2 and loop3 as measured by reader 510.

Rs530 is the sheet resistance of the material that forms conductor 530.

L1 is length L1 from the end of a conductor that couples to reader 410 to the location where liquid 515 bridges between the conductors.

W530 is the width of conductor 530.

W550 is the width of conductor 550.

The magnitudes of Rloop2 and Rloop3 are known. The values of Rs530, Rs550, W530, and W550 are known. The unknown variable in Equation 7 is L1, so the value of L1 may be determined as shown below.

$$L1=(Rloop2-Rloop3)/((Rs430/W430)-(Rs450/W450)) \quad \text{Equation 8:}$$

The difference of Rloop2 and Rloop3 is non-zero because the resistance of conductor 530 (e.g., R530) is different from the resistance of conductors 540 (e.g., R540) and 550 (e.g., R550). In this implementation, the resistance of conductors 540 and 550 are the same (e.g., R540=R550). In another implementation, the resistances of conductors 530, 540, and 550 may all be different. The differences of (Rs530/W530) and (Rs550W550) is also likely non-zero because the resistance of conductors 530 and 550 are different because their sheet resistances are different or their widths are different.

Substituting the known values into Equation 8 provides the value of L1, which is the distance from the end of the conductors coupled to reader 510 to the position of liquid 515 along a length of the conductors. Using the above method, according to various aspects of the present invention, a system for detecting moisture may detect the presence of moisture (e.g., liquid) using at least two conductors and the relative position of the liquid using at least three conductors.

The above method and equations may be used with three or more conductors. Any number of equations may be drafted to determine the length L1. In the above example, had liquid spread to conductor 560, equations could have been drafted, as shown above, that included conductor 560.

It is better to develop equations for adjacent conductors, such as loop2 and loop3, as opposed to non-adjacent conductors, such as loop1, because according to various aspects of the present invention, taking the difference of equations of adjacent conductors results in cancelling out the resistors (e.g., RL1, RL2) due to the liquid (e.g., 515). The cancellation, or subtraction, of the resistors due to the liquid, assumes that the resistivity and volume of the liquid is substantially uniform in the area where the liquid contacts the conductors and that the conductors are evenly spaced apart from each other.

As discussed above, a moisture detecting system may detect the presence of moisture with two conductors and the position of the liquid, with respect to the length of the conductors, with three conductors. A system may use four conductors, as shown in FIGS. 2-5, to provide redundancy. Redundancy may be used to verify that the system is functioning properly or to verify a measurement. Additional conductors provide additional adjacent paths for measuring the resistance of a loop. Regardless of the number of conductors available, at least one conductor of the loops measured should have a total resistance that is different from the total resistance of the other conductors of the loops measured. For example, referring to FIG. 5, the resistance of conductor 530 (e.g., R1) is different from the resistance of conductors 540 and 550 (e.g., R2), so loop2 and loop3 may be used to detect the position of the liquid. The resistance of conductor 560 (e.g., R1) is different from the resistance of conductors 540 and 550 (e.g., R2), so loop3 and a loop through conductor 550, the liquid (not shown), and conductor 560 may be used to detect the position of the liquid.

As discussed above, the conductor spacing and/or substrate material may be selected to facilitate the spreading of a liquid between conductors and not along a length of a single conductor. The uniformity of the value of the resistance of the liquid between conductors is enhanced when the liquid spreads across the conductors in substantially the same location as opposed to running along one or more conductors before spreading to the other conductors. Having the liquid spread between the conductors in substantially the same position along the length of the conductors improves the accuracy of determining the position of the liquid along the length of the conductor.

Figure 6:
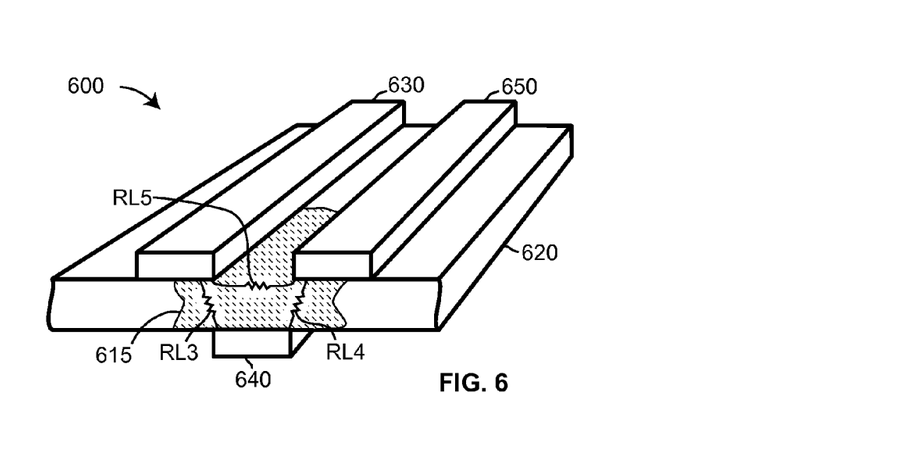
FIG. 6 is a perspective plan view of another implementation of a substrate and conductors of a moisture detector.

In another implementation, conductors and substrate 600 of FIG. 6, includes conductors 630, 640, and 650 coupled to substrate 620. Conductors 630, 640, and 650 run parallel to each other. Conductors 630 and 650 are positioned on one side of substrate 620 and conductor 640 is position on the other side of substrate 620. The distance between each conductor is the same, so conductor 630 is the same distance from conductor 640 and 650 and conductor 640 is the same distance from conductor 650. The substrate is absorbent. The distance between conductor 640 and 630 and conductor 640 and 650 may be the same as the distance between conductor 630 and 650 when substrate 620 contains or is saturated with a liquid.

Absent a liquid, for example liquid 615, in substrate 620 the impedance between the conductors is infinite (e.g., open circuit). When liquid is absorbed by substrate 620, the conductivity of the liquid establishes impedance (e.g., resistances) RL3, RL4, and RL5 between conductors 630 and 640, conductors 640 and 650, and conductors 630 and 650 respectively.

As discussed above, the resistance of conductor 630 is different from the resistance of conductors 640 and 640 or the resistance of all conductors 630, 640, 650 are different. Because the distance between the conductors is about the same and the conductivity of the liquid is likely uniform in the proximity of the conductors, the magnitudes of RL3, RL4, and RL5 are about the same.

The resistance of two loops of conductors and substrate 600 may be measured and the difference of the loops taken to determine the position of liquid as discussed above. The distance between the conductors, including the thickness of substrate 620, and the material of substrate 620 may be selected so that liquid has the propensity to spread (e.g., bridge) between the conductors at a location rather than traveling (e.g., seeping) along the length of a conductor.

Conductor placement on the substrate may permit locating the position of a liquid relative to the substrate. In an implementation, conductors, such as separate and electrically not connected instances of conductors 230-260, may be organized as groups positioned at different locations on the substrate. A substrate may include one or more groups of conductors. A group of conductors may be positioned a distance away from another group of conductors. Detecting a liquid with one group, but not another may provide an indication of the location of the liquid relative to the substrate. Detecting a liquid by one or more groups may indicate the area of the substrate covered by the liquid.

In another implementation, conductor separation may be used to separate the area of a substrate into zones. For example, in system 700, referring to FIG. 7, the space between conductors 730, 740, and 750 is greater in zones 760, 762, and 764 than in zones 770 and 772. Increased spacing between conductors decreases the likelihood that liquid will spread to contact all three conductors, so the likelihood of detecting liquid in zones 760, 762, and 764, even though it may be present, is reduced. The closer spacing between conductors 730, 740, and 750 in zones 770 and 772 increases the likelihood that a liquid will spread between all three conductors thereby providing the opportunity to detect the presence and location of the liquid. When a substrate is split into zones, detecting the position of a liquid relative to the length of the conductors may be of less importance than merely detecting the presence of the liquid. A substrate with zones of small area (e.g., high granularity) may decrease the importance of determining the position of the liquid in the zone. A substrate with zone of larger area may benefit from detecting zone and position in the zone using the method discussed above. In either case, detecting the position of the liquid along a conductor, as discussed above, may be used to detect the zone where a liquid is positioned.

Figure 7:
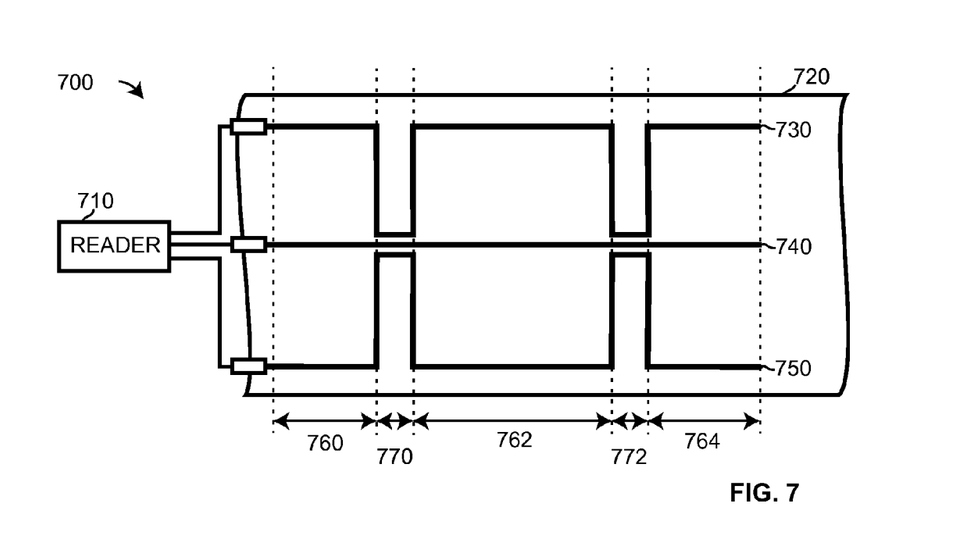
FIG. 7 is a top plan view of another implementation of a moisture detector that includes zones according to various aspects of the present invention.

In the implementation of FIG. 7, decreasing the likelihood of detecting liquid in zones 760, 762, and 764 decreases the granularity of the position determined by reader 710. The position of liquid may most likely be detected in zones 770 and 772 and less likely in zones 760, 762, and 764. Because reader 710 is positioned on the left side of the substrate and conductors, the difference in resistance, referring to Equation 6, in zone 770 will be less than the difference in resistance in zone 772 because the distance from reader 710 to zone 770 is less than the distance from reader 710 to zone 772. Detecting the zone where the liquid is located, as opposed to the length along a conductor, is a more simple calculation and may be performed by a comparator rather than using a processing circuit that includes a microprocessor.

Zones may also be created by insulating (e.g., coating, protecting, sheathing, encasing) the conductors in the zones where liquid is not to be detected and left uninsulated (e.g., exposed, unprotected), as discussed above, in zones where detecting liquid is desirable.

Figure 8:
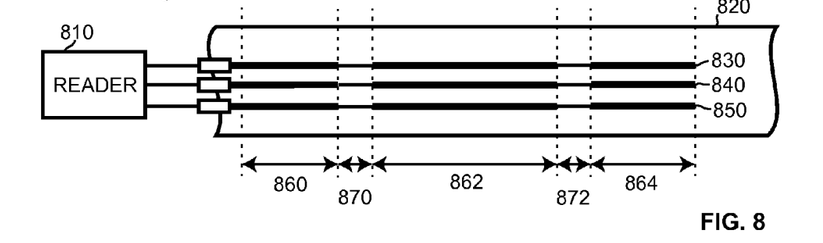
FIG. 8 is a top plan view of another implementation of a moisture detector according to various aspects of the present invention.

For example, in system 800 of FIG. 8, two or more, preferably all, of conductors 830, 840, and 850 may be insulated in zones 860, 862, and 864. The conductor spacing in zones where the conductors are insulated in unimportant, so they may be closely or broadly spaced. In the zones where detecting liquid is desired, conductors 830, 840, and 850 may be left uninsulated and are spaced, as discussed above, to facilitate the spread of liquid between the conductors. As liquid spreads across the substrate, only those areas where the conductors are uninsulated will permit the reader to detect the presence and/or position of the liquid. As discussed above, creating zones may result in simplifications of reader 810.

Conductor separation may be combined with conductor insulating to create zones. Zones may be used to exclude portions of an area from detecting a liquid.

Resistive wire may perform the function of a conductor as discussed above. A covering of a resistive wire may perform the function of a substrate as discussed above. A resistive wire includes a wire (e.g., strip) that has a known resistance per length. Resistance per length may be expressed as ohms per circular mil foot (e.g., ohms/CMF, $\Omega$/CMF), which is the resistance in ohms of a wire that is one foot in length and 1 mil (e.g., 0.001 inch) in diameter. For example, an alloy of 55% copper and 45% nickel that is 0.01 inches in diameter has a resistive value of 2.94 ohms per foot at 68 degrees Fahrenheit.

A resistive wire may be encased (e.g., sheathed) in an absorptive material to retain liquid between the wires to establish resistances between the wires for detecting the presence and position of a liquid. A material that encases a resistive wire may perform the functions of a substrate as discussed above. For example, referring to FIGS. 9-10, resistive wires 930, 940, and 950 are sheathed in absorptive material 932, 942, and 952 and positioned proximate to each other. The wires may be twisted around each other to help them retain their position relative to each other. A reader, not shown, may be coupled to the wires. Conductive liquid 1015 enters absorptive material 932, 942, and 952 to establish resistances RL6, RL7, and RL8 between conductors 930, 940, and 950. A reader may detect the presence of liquid 1015 and/or the location of liquid 1015 along a length of the resistive wires as discussed above. The resistance (e.g., per unit length, total) of at least one of the resistive wires (e.g., conductors) should be different than the resistance of the other wires. A resistive wire may have a different resistance by having a different diameter or being formed of a different material. It is assumed that the length of the resistive wires is all about the same.

Figure 9:
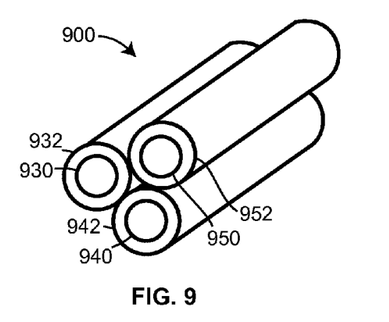
FIG. 9 is a perspective plan view of another implementation of a substrate and conductors of a moisture detector according to various aspects of the present invention.
Figure 10:
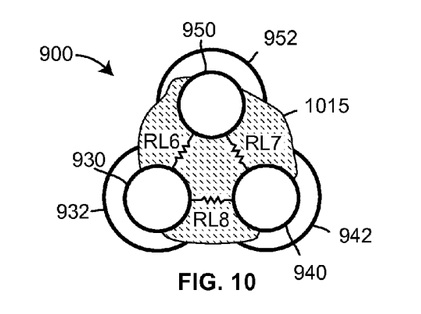
FIG. 10 is a side view plan the substrate and conductors FIG. 9 in the presence of moisture.

As discussed above, it is preferred for a reader to read a loop formed of adjacent conductors. In configuration 900, each wire is adjacent to the other two wires, so loops may be formed between any two wires. Zones may be formed along the length of conductive wires by using non-absorptive sheathing to form zones where liquid cannot be detected and zones using absorptive sheathing to form zones where liquid may be detected.

The area of a substrate may also be separated into zones by varying the resistance of a conductor in accordance with one or more locations with respect to the substrate. The variation in the impedance (e.g., resistance) of a conductor may be linear. Conductors having a sheet resistance were discussed above. The variation, moving from one end (e.g., left) to the other end (e.g., right), of a conductor having a sheet resistance is linear as long as the sheet resistance and width of the conductor remain constant along the length of the resistance.

Variation of the resistance of a conductor may be stepwise. A step-wise variation occurs when the resistance from one location in a conductor to a next proximate location changes by a unit. For example, movement from left to right by an amount may result in a unit increase in resistance. A change in resistance may be accomplished by changing the material that forms the conductor, changing a width of the conductor, changing a sheet resistance of the conductor, or inserting a resistance (e.g., component) into the conductor.

Changing a material of the conductor to vary the resistance of the conductor may be accomplished by forming a portion of the length of the conductor of one material and a portion of the next length of the conductor of another material that has a different resistive value (e.g., sheet resistance). The material of the conductor may alternate along a length of the conductor so that a first material is followed by a second material that is followed by the first material and so forth. Any number of different materials may be placed in series to vary the resistance of a conductor.

A resistive wire, as discussed above, may be formed of different materials in series to accomplish step-wise changes in resistance along a length of the wire.

In another implementation, resistors may be inserted into a conductor by inserting resistors, in whatever form, between segments of the conductor so that the resistors are in series with the conductor along its length.

Figure 11:
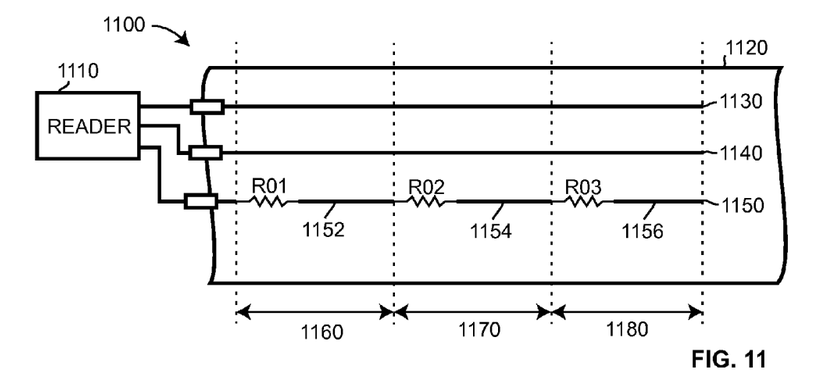
FIG. 11 is a top plan view of another implementation of a moisture detector that includes zones according to various aspects of the present invention.

For example, system 1100 of FIG. 11 includes reader 1110, substrate 1120, and conductors 1130-1150. Reader 1110 couples to the conductors at a left side of substrate 1120 with references to FIG. 11.

Conductors 1130 and 1140 are formed of a material having a sheet resistance as discussed above. Conductors 1130 and 1140 extend from a left side, with respect to FIG. 11, of substrate 1120 to a right side of substrate 1120. Because conductors 1130 and 1140 are formed of a material having a sheet resistance and, in this implementation, have a constant width, the resistance of conductor 1130 or conductor 1140 is substantially the same and increases linearly along the length of the conductor. Conductor 1130 may have the same resistance (e.g., same sheet resistance and width) as conductor 1140 or the resistance of conductor 1130 may be different (e.g., different sheet resistance, different materials, different width) from the resistance of conductor 1140. As discussed above, they are the same in this implementation.

Conductor 1150 is formed of different segments coupled in series. In an implementation, segments 1152-1156 are formed of a same material. The material of segments 1150-1156 may be of the same material as the material used to form conductor 1130 or conductor 1140. Segments R01-R03 are formed of a material that has a different, preferably higher, resistance than the resistance of segments 1152-1156. A different resistance may include a different sheet resistance and/or a different total resistance for the length of segments R01-R03.

Segments R01-R03 may be formed of a material that is different from the material used to form segments 1152-1156 and/or conductors 1130 and 1140. Segments R01-R03 may be formed of the same material used to form segments 1152-1156 and/or conductors 1130 and 1140. Segments R01-R03 may be formed of a same or different material having a different physical structure (e.g., thickness, width) than segments 1152-1156 and/or conductors 1130 and 1140. Segments R01-R03 may be formed of a resistive component (e.g., chip, axial metal oxide, metal film MELF, carbon composite molded, wire-wound, thick film, ceramic, metal foil) coupled in series with proximate segments of segments 1152-1156.

In an implementation, the magnitude of the resistance of conductor 1130, conductor 1140, and the whole of segments 1152-1156 is less than the expected magnitude of the resistance of possible liquids that are likely to contact conductors 1130-1150. The magnitude of the resistance of each segment R01-R03 is greater than the magnitude of the resistance of possible liquids that are likely to contact conductors 1130-1150.

For example, the bulk resistance (e.g., rho) of blood varies between 150-400 ohms-centimeter (e.g., $\Omega$-cm). As discussed above, the separation between the conductors, the thickness of the substrate, and the absorbency of the substrate may be used to influence (e.g., shape, control) the volume of blood that contacts the conductors and the magnitude of the resistance (e.g., RL) of the blood between conductors.

The sheet resistance of conductors 1130-1150, in this implementation, is less than the expected sheet resistance of the blood that comes into contact with conductors 1130-1150. The sheet resistance of conductors 1130-1150 may be significantly less (e.g., 1-2 orders of magnitude) less than the expected sheet resistance of blood that contacts the conductors and substrate. Segments 1152-1156 may have the same sheet resistance as conductors 1130 and 1140. Conductors 1130-1140 and segments 1152-1156 may be spaced apart from each other and have physical dimensions (e.g., width, thickness) so that the total resistance of conductors 1130-1140 and segments 1152-1156 are less than the resistance of blood (e.g., RL1-RL4) between the conductors and/or segments. The magnitude of the resistance of segments R01-R03 is more than the resistance of blood (e.g., RL1-RL4) between the conductors and/or segments.

Figure 12:
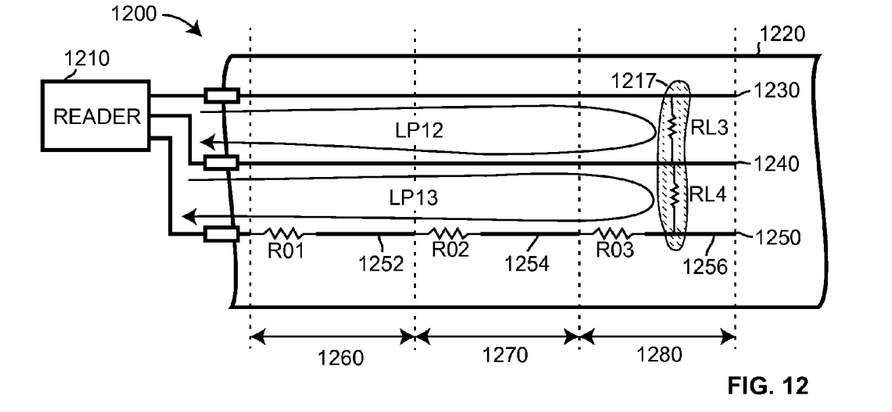
FIG. 12 is a top plan view of the moisture detector of FIG. 11 in the presence of moisture.

The presence and position of a liquid proximate to conductors 1130-1150 may be determined as discussed above. Liquid 1217 forms resistance RL3 between conductors 1130 and 1140 and resistance RL4 between conductance 1140 and 1150. Reader 1110 applies a voltage across conductors 1130 and 1140, measures the current that flows, and calculates the impedance of loop lp12. The impedance of loop lp12 may be expressed as:

$$Rlp12 = R1130 + RL3 + R1140, \text{ where} \qquad \text{Equation 9:}$$

Rlp12: is the impedance along the loop from reader 1110 along length of conductor 1130 to the location of liquid 1217, through the impedance RL3 of liquid 1217, and along the length of conductor 1140 from the location of liquid 1217 back to reader 1110.

R1130 is the impedance of conductor 1130 along its length from reader 1110 to the location of liquid 1217.

RL3 is the impedance through liquid 1217 between conductor 1130 and conductor 1140.

R1140 is the impedance of conductor 1140 along its length from the location of liquid 1217 to reader 1110.

Reader 1110 applies a voltage across conductors 1140 and 1150, measures the current that flows, and calculates the impedance of loop lp13. The impedance of loop lp13 may be expressed as:

$$Rlp13 = R1140 + RL4 + R1156 + R03 + R1154 + R02 + R112 + R01, \text{ where} \qquad \text{Equation 10:}$$

Rlp13: is the impedance along the loop from reader 1110 along length of conductor 1140 to the location of liquid 1217, through the impedance RL4 of liquid 1217, and along the length of conductor 1150 from the location of liquid 1217, through segments 1152-1156 and R01-R01, back to reader 1110.

R1140 is the impedance of conductor 1140 along its length from reader 1110 to the location of liquid 1217.

RL4 is the impedance through liquid 1217 between conductor 1140 and segment 1156 of conductor 1150.

R1056, R1054, and R1052 are the impedances of segments 1156, 1154, and 1152 of conductors 1150 from the location of liquid 1217 to reader 1110.

R03, R02, R01 are the impedances of segments R01, R02, and R03 of conductor 1150.

Assume, for this example, that the impedance (e.g., resistance) of segments R01, R02, and R03 are the same such that:

$$R\text{comp} = R01 = R02 = R03. \qquad \text{Equation 11:}$$

Further, assume that the distance between conductor 1130 and conductor 1140 is the same as the distance between conductors 1140 and 1150. Further assume that the conductivity of liquid 1217 is fairly uniform, so that the magnitude of RL3 is about the same as the magnitude of RL4, so that:

$$RL = RL3 = RL4. \qquad \text{Equation 12:}$$

Subtracting Equation 10 from Equation 9 and substituting the equivalent values expressed in Equations 11 and 12 yields:

$$Rlp12 - Rlp13 = R1130 + RL + R1140 - (R1140 + RL + R1156 + R1154 + R1152 + 3*R\text{comp}) \qquad \text{Equation 13:}$$

Equation 13 simplifies to:

$$Rlp12 - Rlp13 = R1130 - (R1156 + R1154 + R1152 + 3*R\text{comp}) \qquad \text{Equation 14:}$$

If the sum of the magnitude of the resistances of segments 1152-1156 is the same as the magnitude of total resistance of conductor 1130, a further simplification may be made. Factors that provide the same magnitude of resistance include sheet resistance, width, thickness and individual lengths of segments 1152-1156. Assuming that R1130 is substantially equal to (R1156+R1154+R1152), Equation 14 simplifies to:

$$Rlp13-Rlp12=3*Rcomp \qquad \text{Equation 15:}$$

The difference of the magnitude of the resistances of the loop lp12 and loop lp13 is the number of resistive segments (e.g., R01, R02, R03) between reader 1110 and position of liquid 1217. Using resistive segments, and in this implementation resistive components with a higher resistance than conductors 1130 and 1140, segments 1152-1156, and the expected resistance of the liquid simplifies the calculation resulting in potential simplifications in the circuitry use to implement reader 1110.

Using the analysis discussed above, the difference (e.g., Rlp13-Rlp 12) between the resistance (e.g., Rlp13) of loop lp13 and the resistance (e.g., Rlp12) of loop lp12 for a liquid that spans conductors 1130, 1140, and segment 1154 in zone 1170 is, in its simplified form using the assumptions discussed above:

$$Rlp13-Rlp12=2*Rcomp \qquad \text{Equation 16:}$$

Analysis for a liquid that spans conductors 1030, 1040, and segment 1052 in zone 1160 is, in its simplified form using the same assumptions discussed above:

$$Rlp13-Rlp12=1*Rcomp \qquad \text{Equation 17:}$$

The above shows that the multiplier (e.g., 1, 2, 3) of the resistive component (e.g., R01, R02, R03, Rcomp) corresponds to the distance of the resistive component from reader 1110. Further, the resistive components may be considered to separate substrate 1120 into zones. The area of substrate 1120 from resistive element R01 to resistive element R02 corresponds to zone 1160, from resistive element R02 to resistive element R03 corresponds to zone 1170, and to the right of resistive element R03 corresponds to zone 1180. As discussed above, the presence of liquid in zone 1160 will result in reader 1110 detecting the magnitude of resistance of one resistive element, the presence of liquid in zone 1170 will result in reader 1110 detecting the magnitude of resistance of two resistive elements, and so forth as demonstrated above.

Reader 1110 detects liquid only in the most proximate zone. In a situation where liquid spans conductors 1130, 1140, segment 1152, and segment 1154 and/or K56, reader 1110 would detect only the presence of liquid in zone 1160 and not in zone 1170 and/or 1180. However, as will be discussed in further detail below, reader 1110 is not limited to coupling to only one end of the conductors 1130-1150 or to one side (e.g., left, right) of substrate 1120. Reader 1110 may couple to left end, referring to FIGS. 11-12, of conductors 1130-1150, the right end, or to both ends simultaneously. Reader 1110 may further couple to a portion of conductors 1130-1150 that is way from either end using leads (e.g., conductors, wires, traces) that are not affected by the presence of a liquid.

Conductors 1130 and 1140, segments 1152-1156, and resistive segments R01-R03 may be printed on substrate 1120 using resistive inks. A process capable of printing different areas of substrate 1120 with different materials is suitable for printing conductors 1130 and 1140, segments 1152-1156, and resistive segments R01-R03. For example, a two-step printing process may be used that prints conductor 1130, conductor 1140, and segments 1152-1156 in one step of one material and resistive segments R01-R03 of a different material in another step.

Figure 13:
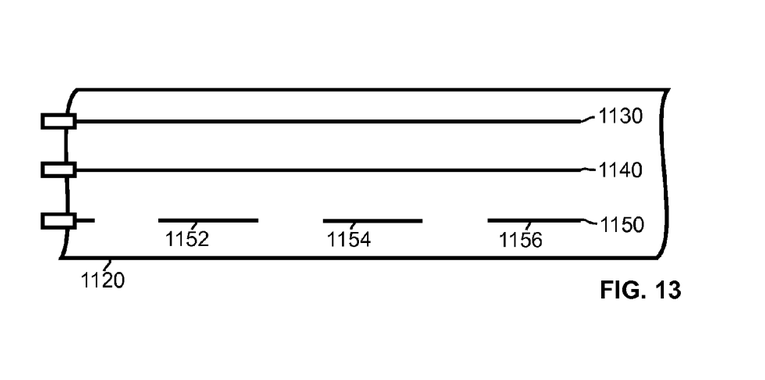
FIG. 13 is a top plan view a partially printed substrate and conductors of the moisture sensor of FIG. 11.
Figure 14:
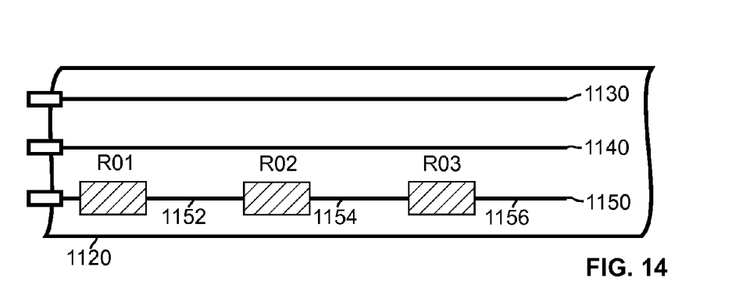
FIG. 14 is a top plan view a printed substrate and conductors of the moisture sensor of FIG. 11.

For example, referring to FIG. 13, in a step of a printing process, substrate 1120 is printed with conductor 1130, conductor 1140, and segments 1152-1156. In another step, referring to FIG. 14, resistive segments R01-R03 are printed. The steps may be performed in any order and/or repeated any number of times. Conventional processes for printing conductive ink may be used.

In another method of manufacturing a substrate and conductors of a moisture sensor, a manufacturing step prints, deposits, or forms conductor 1130, conductor 1140, and segments 1152-1156. In another manufacturing step, resistive components (e.g., resistors) R01-R03 are positioned, mechanically coupled to substrate 1120, and electrically coupled to a tab of the substrate and/or segments 1152-1156 to form conductor 1150. Conventional manufacturing processes may be used. The steps may be performed in any order.

As discussed above, a moisture detecting system, according to various aspects of the present invention, may detect a location of a liquid relative to a length of a conductor and/or a zone. According to various aspects of the present invention, the conductors and reader discussed above may further perform the function of detecting an area (e.g., spread) of a liquid.

As discussed above, a reader may electrically couple to either end of a conductor used to detect the presence and/or position of a liquid. Refer to FIG. 5, reader 510 detects a location of liquid 515 as length L1 from the left end of conductors 530-550 to the liquid. Coupling reader 510 to the right end of conductors 530-550, reader 510 may detect length L2 which is the distance from the right end of conductors 530-550 to liquid 515. In FIG. 5, length L1 and L2 measure from their respective ends of conductors 530-550 to approximately the middle of the body of liquid 515. Measuring to the middle of the body of liquid E15 is an approximation used for developing the equations.

The flow of a current provided by a reader may travel many paths through a liquid from one conductor to another conductor. When the spread of a liquid is small, the current may travel through the middle portion of the liquid. In accordance with the distance between the conductors, the thickness of the substrate, composition of the liquid, the level of saturation of the substrate, and the width (e.g., spread) of the liquid, the liquid may travel from one conductor to another conductor closer to the edge of the spread of liquid.

Figure 15:
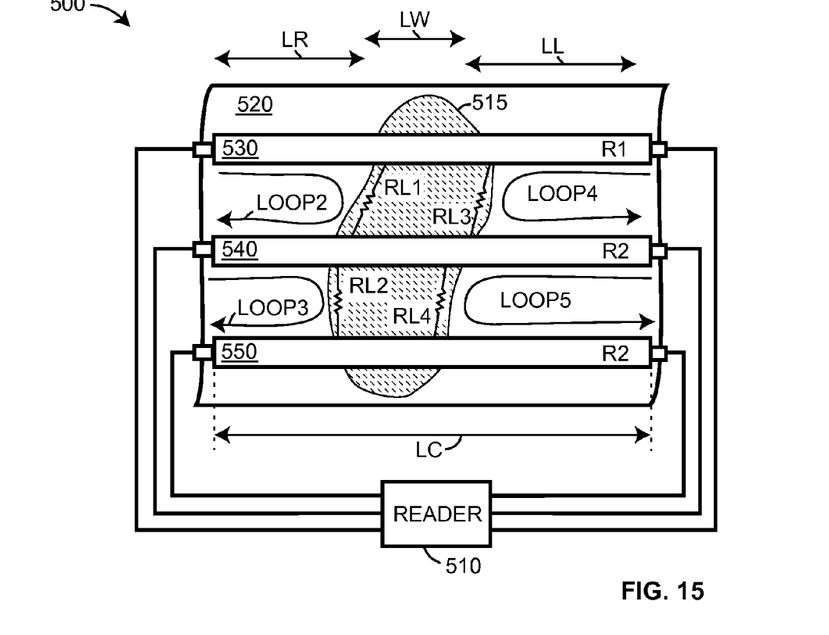
FIG. 15 is a top plan view of an implementation of a moisture detector according to various aspects of the present invention.

Referring to FIG. 15, resistances RL1 and RL2 represent a possible path of a current provided by reader 510 from the left side of conductors 530-550. Resistances RL1 and RL2 are located on a left portion of liquid 515. Resistances RL3 and RL4 represent a possible path of a current provided by reader 510 from the right side of conductors 530-550. Resistances RL3 and RL4 are located on a right portion of liquid 515.

The length of conductors 530-550 are LC. The distance from the left side of conductors 530-550 to resistances RL1 to RL2 is about a distance of RL. As can be seen in FIG. 15, because of the shape of the spread of liquid 515, resistance RL1 is position to the right of resistance RL2, so the distance LR is somewhere between the possible path of the current from conductor 530 to conductor 540 and the possible path of the current from conductor 540 to conductor 550. The same analysis applies to length 12, which is somewhere between the possible paths of current between the conductors. The amount of error in length LR decreases as the spread of liquid 515 increases. Further, the distance between the conductors and the mobility of a liquid through substrate 520 may cooperate to reduce the spread of liquid 515 along the lengths of conductors.

Reader 510 may apply voltages to the left end of conductors 530-550, as discussed above, to determine distance LR. Reader 510 may apply voltages to the right ends of conductors 530-550 through loop4 and loop5, analogous to the method used on the left side, to determine distance 12. Distances LR and 12 may be subtracted for the length of the conductors, LC, to determine the width LW of liquid 515.

Reading from the left and right ends of conductors formed of resistive wires may also be used to determine the area a liquid.

Figure 16:
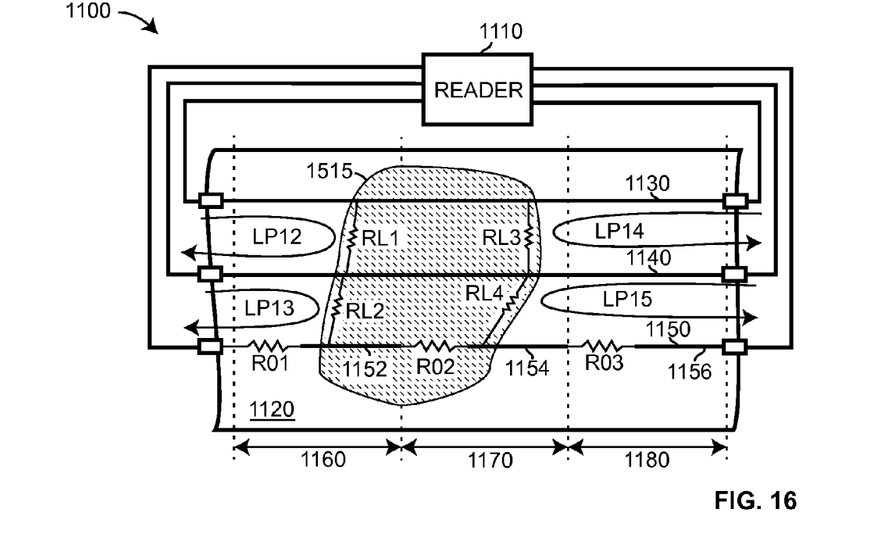
FIG. 16 is a top plan view of another implementation of a moisture detector according to various aspects of the present invention.

Reading from both ends of conductors may also provide information as to the spread of a liquid in terms of zones. As discussed above and referring to FIG. 16, segments R01-R03 split substrate 1120 in zones 1160-1180. When reader 1110 applies a voltage to the left end of conductors 1130-1150, similar to the situation discussed above, reader 1110 detects a single resistive segment R01. Detecting a single resistive segment R01 indicates that liquid is present in zone 1. When reader 1110 applies a voltage to the right end of conductors 1130-1150 via loops lp14 and lp15, reader 1110 detects a single resistive segment R03. Because of the layout of the resistive elements R01-R03 with respect to the zones, detecting a single resistive element from the right side indicates that there is no liquid in zone 1180, but there is liquid in zone 1170. Reader 1110 may then determine that liquid is present in zones 1160 and 1170. With knowledge of an area of a zone, an estimate of the area of the liquid may be made.

The foregoing description discusses preferred embodiments of the present invention, which may be changed or modified without departing from the scope of the present invention as defined in the claims. Examples listed in parentheses may be used in the alternative or in any practical combination. As used in the specification and claims, the words 'comprising', 'including', and 'having' introduce an open ended statement of component structures and/or functions. In the specification and claims, the words 'a' and 'an' are used as indefinite articles meaning 'one or more'. When a descriptive phrase includes a series of nouns and/or adjectives, each successive word is intended to modify the entire combination of words preceding it. For example, a black dog house is intended to mean a house for a black dog. While for the sake of clarity of description, several specific embodiments of the invention have been described, the scope of the invention is intended to be measured by the claims as set forth below. In the claims, the term "provided" is used to definitively identify an object that not a claimed element of the invention but an object that performs the function of a workpiece that cooperates with the claimed invention. For example, in the claim "an apparatus for aiming a provided barrel, the apparatus comprising: a housing, the barrel positioned in the housing", the barrel is not a claimed element of the apparatus, but an object that cooperates with the "housing" of the "apparatus" by being positioned in the "housing".

What is claimed is:

1. A system for cooperating with a provided reader to detect a position of a liquid, the system comprising:
    a first conductor, a second conductor, and a third conductor;
    a reader; wherein:
    the reader electrically couples to a first end portion of the first conductor, a first end portion of the second conductor, and a first end portion of the third conductor respectively;
    a magnitude of an impedance of the first conductor is different from a magnitude of an impedance of the second conductor and a magnitude of an impedance of the third conductor;
    in the absence of the liquid, the first conductor, the second conductor, and the third conductor do not electrically couple to each other;
    the reader determines a magnitude of a first resistance, the magnitude of the first resistance comprises a magnitude of a resistance of a portion of the first conductor, a magnitude of a resistance of the liquid between the first conductor and the second conductor, and a magnitude of a resistance of a portion of the second conductor;
    the reader determines a magnitude of a second resistance, the magnitude of the second resistance comprises the magnitude of the resistance of the portion of the second conductor, a magnitude of a resistance of the liquid between the second conductor and the third conductor, and a magnitude of a resistance of a portion of the third conductor;
    the reader takes a difference between the magnitude of the first resistance and the magnitude of the second resistance to determine the position of the liquid relative to the first end portion of at least one of the conductors.

2. The system of claim 1 wherein a distance between the first conductor and the second conductor is about the same as a distance between the second conductor and the third conductor.

3. The system of claim 1 wherein the reader divides the difference of the magnitude of the first resistance and the magnitude of the second resistance by the difference of the sheet resistance of the first conductor divided by the width of the first conductor and the sheet resistance of the third conductor divided by the width of the third conductor.

4. The system of claim 1 further comprising a substrate, wherein the conductors mechanically couple to the substrate.

5. A system for detecting a position of a liquid, the system comprising:
    a first conductor, a second conductor, a third conductor;
    a substrate; and
    a reader; wherein:
    the conductors couple to the substrate;
    the reader electrically couples to a first end portion of the first conductor, a first end portion of the second conductor, and a first end portion of the third conductor respectively;
    a magnitude of an impedance of the first conductor is different from a magnitude of an impedance of the second conductor and a magnitude of an impedance of the third conductor;
    in the absence of the liquid, the first conductor, the second conductor, and the third conductor do not electrically couple to each other;
    the reader determines a magnitude of a first resistance, the magnitude of the first resistance comprises a magnitude of a resistance of a portion of the first conductor, a magnitude of a resistance of the liquid between the first conductor and the second conductor, and a magnitude of a resistance of a portion of the second conductor;

the reader determines a magnitude of a second resistance, the magnitude of the second resistance comprises the magnitude of the resistance of the portion of the second conductor, a magnitude of a resistance of the liquid between the second conductor and the third conductor, and a magnitude of a resistance of a portion of the third conductor;

the reader takes a difference between the magnitude of the first resistance and the magnitude of the second resistance to determine the position of the liquid relative to the first end portion of at least one of the conductors.

6. The system of claim 5 wherein the conductors couple to a first side of the substrate.

7. The system of claim 5 wherein the first conductor is space a first distance away from at least one of the second conductor and the third conductor.

8. The system of claim 5 wherein:

the first conductor is space a first distance away from the second conductor;

the first conductor is space a second distance away from the third conductor.

\* \* \* \* \*